United States Patent
Davis et al.

(10) Patent No.: US 12,109,290 B2
(45) Date of Patent: Oct. 8, 2024

(54) HAIR SHINE COMPOSITIONS

(71) Applicant: KAO USA Inc., Cincinnati, OH (US)

(72) Inventors: Amy Davis, Cincinnati, OH (US); Elisabeth Cox, Cincinnati, OH (US)

(73) Assignee: KAO USA INC., Cincinnati, OH (US)

( * ) Notice: Subject to any disclaimer, the term of this patent is extended or adjusted under 35 U.S.C. 154(b) by 200 days.

(21) Appl. No.: 17/563,750

(22) Filed: Dec. 28, 2021

(65) Prior Publication Data
US 2022/0202679 A1 Jun. 30, 2022

Related U.S. Application Data

(60) Provisional application No. 63/131,420, filed on Dec. 29, 2020.

(51) Int. Cl.
*A61K 8/49* (2006.01)
*A61K 8/34* (2006.01)
*A61Q 5/00* (2006.01)
*A61Q 5/02* (2006.01)

(52) U.S. Cl.
CPC ............ *A61K 8/4973* (2013.01); *A61K 8/345* (2013.01); *A61Q 5/00* (2013.01); *A61Q 5/02* (2013.01); *A61K 2800/30* (2013.01)

(58) Field of Classification Search
None
See application file for complete search history.

(56) References Cited

U.S. PATENT DOCUMENTS

| | | | |
|---|---|---|---|
| 9,603,788 B2 | 3/2017 | Mimura et al. | |
| 9,861,645 B2 | 1/2018 | Kazin et al. | |
| 9,918,923 B1 | 3/2018 | Naiberk et al. | |
| 10,123,966 B2 | 11/2018 | Mahmud et al. | |
| 10,463,596 B1 | 11/2019 | Custer et al. | |
| 2006/0057081 A1 | 3/2006 | Boxrud | |
| 2014/0187518 A1 | 7/2014 | Kazin et al. | |
| 2016/0158261 A1 | 6/2016 | Friedman et al. | |
| 2017/0056307 A1* | 3/2017 | Soeberdt | A61K 8/42 |
| 2017/0216177 A1 | 8/2017 | Thrower | |
| 2019/0167548 A1 | 6/2019 | Goutsis et al. | |
| 2020/0214953 A1 | 7/2020 | Lane | |

FOREIGN PATENT DOCUMENTS

WO 20180163176 A1 9/2018

OTHER PUBLICATIONS

Kuraray America. "Isopentyldiol: The Multi-Functional Ingredient for all formulations & all formulators" <https://www.cosmeticsandtoiletries.com/formulas-products/hair-care/article/21835776/kuraray-america-isopentyldiolthe-multi-functional-ingredient-for-all-formulations-all-formulators> May 29, (Year: 2020).*
Unknown: "Isopentyldiol the multi functional ingredient for Personal Care", Mar. 1, 2018 (Mar. 1, 2018), pp. 1-31, XP055913948, Retrieved from the Internet: 3,13 URL:http://www.lhanskorea.com/html/_skin/2, /brochure/IPD Product%20summary_incosmetics%20Global%2O2O18.pdf [retrieved on Apr. 20, 2022] p. 8-p. 13.
International Search Report and Written Opinion for International application No. PCT/US2021/065357 dated Apr. 29, 2022.

* cited by examiner

*Primary Examiner* — Nicole P Babson
(74) *Attorney, Agent, or Firm* — Dinsmore & Shohl LLP (57) ABSTRACT

Hair shine compositions are disclosed. In embodiments, a hair shine composition may include greater than or equal to 50 wt/wt % and less than or equal to 95 wt/wt % water; greater than or equal to 0.5 wt/wt % and less than or equal to 3 wt/wt % propanediol; and greater than or equal to 0.25 wt/wt % and less than or equal to 2 wt/wt % dimethyl isosorbide. In embodiments, a wt/wt % ratio of propanediol to dimethyl isosorbide may be from 1.00:1 to 3.00:1.

20 Claims, 2 Drawing Sheets

HAIR SHINE COMPOSITIONS

CROSS-REFERENCE TO RELATED APPLICATIONS

The present specification claims the benefit of U.S. Provisional Application Ser. No. 63/131,420 filed Dec. 29, 2020 and entitled "Hair Shine Compositions," the entirety of which is incorporated by reference herein.

FIELD

Embodiments of the present disclosure are generally related to hair compositions, and are specifically related to hair shine compositions that impart a relatively high refractive index and strength.

TECHNICAL BACKGROUND

Consumers of hair care products desire compositions that impart shine along with moisturizing properties. However, conventional hair compositions do not impart the amount of shine and strength desired by the consumer.

Accordingly, a need exists for alternative hair compositions that produce the desired amount of shine and strength while delivering moisturizing properties.

SUMMARY

According to a first aspect A1, a hair shine composition may comprise: greater than or equal to 50 wt/wt % and less than or equal to 95 wt/wt % water; greater than or equal to 0.5 wt/wt % and less than or equal to 3 wt/wt % propanediol; and greater than or equal to 0.25 wt/wt % and less than or equal to 2 wt/wt % dimethyl isosorbide, wherein: a wt/wt % ratio of propanediol to dimethyl isosorbide is from 1.00:1 to 3.00:1.

A second aspect A2 includes the hair shine composition according to the first aspect A1, wherein the wt/wt % ratio of propanediol to dimethyl isosorbide is from 1.25:1 to 1.75:1.

A third aspect A3 includes the hair shine composition according to the first aspect A1 or the second aspect A2, wherein the hair shine composition further comprises greater than or equal to 0.25 wt/wt % and less than or equal to 2 wt/wt % isopentyldiol.

A fourth aspect A4 includes the hair shine composition according to any one of the first through third aspects A1-A3, wherein the hair shine composition comprises greater than or equal to 0.5 wt/wt % and less than or equal to 2.5 wt/wt % propanediol.

A fifth aspect A5 includes the hair shine composition according to any one of the first through fourth aspects A1-A4, wherein the hair shine composition comprises greater than or equal to 0.3 wt/wt % and less than or equal to 1.75 wt/wt % dimethyl isosorbide.

A sixth aspect A6 includes the hair shine composition according to any one of the first through fifth aspects A1-A5, wherein the hair shine composition comprises greater than or equal to 50 wt/wt % and less than or equal to 75 wt/wt % water.

A seventh aspect A7 includes the hair shine composition according to any one of the first through fifth aspects A1-A5, wherein the hair shine composition comprises greater than or equal to 75 wt/wt % and less than or equal to 95 wt/wt % water.

An eighth aspect A8 includes the hair shine composition according to any one of the first through sixth aspects A1-A6, wherein the hair shine composition is formulated for use as a shampoo.

A ninth aspect A9 includes the hair shine composition according to the eighth aspect A8, wherein the hair shine composition further comprises a non-sulfate cleanser.

A tenth aspect A10 includes the hair shine composition according to the eighth aspect A8 or the ninth aspect A9, wherein the hair shine composition is free of sulfates.

An eleventh aspect A11 includes the hair shine composition according to any one of the first through fifth aspects A1-A5 or the seventh aspect A7, wherein the hair shine composition is formulated for use as a spray.

According to a twelfth aspect A12, a hair shine composition may comprise: greater than or equal to 50 wt/wt % and less than or equal to 95 wt/wt % water; greater than or equal to 0.5 wt/wt % and less than or equal to 15 wt/wt % propanediol; and greater than or equal to 0.1 wt/wt % and less than or equal to 12 wt/wt % dimethyl isosorbide, wherein: a wt/wt % ratio of propanediol to dimethyl isosorbide is from 1.00:1 to 3.00:1.

A thirteenth aspect A13 includes the hair shine composition according to the twelfth aspect A12, wherein the wt/wt % ratio of propanediol to dimethyl isosorbide is from 1.25:1 to 1.75:1.

A fourteenth aspect A14 includes the hair shine composition according to the twelfth aspect A12 or the thirteenth aspect A13, wherein the hair shine composition further comprises greater than or equal to 0.25 wt/wt % and less than or equal to 2 wt/wt % isopentyldiol.

A fifteenth aspect A15 includes the hair shine composition according to any one of the twelfth through fourteenth aspects A12-A14, wherein the hair shine composition comprises greater than or equal to 1 wt/wt % and less than or equal to 13 wt/wt % propanediol.

A sixteenth aspect A16 includes the hair shine composition according to any one of the twelfth through fifteenth aspects A12-A15, wherein the hair shine composition comprises greater than or equal to 0.25 wt/wt % and less than or equal to 10 wt/wt % dimethyl isosorbide.

A seventeenth aspect A17 includes the hair shine composition according to any one of the twelfth through sixteenth aspects A12-A16, wherein the hair shine composition comprises greater than or equal to 50 wt/wt % and less than or equal to 75 wt/wt % water.

An eighteenth aspect A18 includes the hair shine composition according to any one of the twelfth through sixteenth aspects A12-A16, wherein the hair shine composition comprises greater than or equal to 75 wt/wt % and less than or equal to 95 wt/wt % water.

A nineteenth aspect A19 includes the hair shine composition according to any one of the twelfth through seventeenth aspects A12-A17, wherein the hair shine composition is formulated for use as a shampoo.

A twentieth aspect A20 includes the hair shine composition according to the nineteenth aspect A19, wherein the hair shine composition further comprises a non-sulfate cleanser.

A twenty-first aspect A21 includes the hair shine composition according to the nineteenth aspect A19 or the twentieth aspect A20, wherein the hair shine composition is free of sulfates.

A twenty-second aspect A22 includes the hair shine composition according to any one of the twelfth through sixteenth aspects A12-A16 or the eighteenth aspect A18, wherein the hair shine composition is formulated for use as a spray.

Additional features and advantages of the hair shine compositions described herein will be set forth in the detailed description which follows, and in part will be readily apparent to those skilled in the art from that description or recognized by practicing the embodiments described herein, including the detailed description which follows, the claims, as well as the appended drawings.

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate the various embodiments described herein, and together with the description serve to explain the principles and operations of the claimed subject matter.

DETAILED DESCRIPTION

Reference will now be made in detail to various embodiments of hair shine compositions that impart a desired amount of shine, as indicated by a relatively high refractive index, and strength. According to embodiments, a hair shine composition includes greater than or equal to 50 wt/wt % and less than or equal to 95 wt/wt % water; greater than or equal to 0.5 wt/wt % and less than or equal to 3 wt/wt % propanediol; and greater than or equal to 0.25 wt/wt % and less than or equal to 2 wt/wt % dimethyl isosorbide. A wt/wt % ratio of propanediol to dimethyl isosorbide is from 1.00:1 to 3.00:1. According to other embodiments, a hair shine composition includes greater than or equal to 50 wt/wt % and less than or equal to 95 wt/wt % water; greater than or equal to 0.5 wt/wt % and less than or equal to 15 wt/wt % propanediol; and greater than or equal to 0.1 wt/wt % and less than or equal to 12 wt/wt % dimethyl isosorbide. A wt/wt % ratio of propanediol to dimethyl isosorbide is from 1.00:1 to 3.00:1. Various embodiments of hair shine compositions will be described herein with specific reference to the appended drawings.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

Unless otherwise expressly stated, it is in no way intended that any method set forth herein be construed as requiring that its steps be performed in a specific order, nor that with any apparatus specific orientations be required. Accordingly, where a method claim does not actually recite an order to be followed by its steps, or that any apparatus claim does not actually recite an order or orientation to individual components, or it is not otherwise specifically stated in the claims or description that the steps are to be limited to a specific order, or that a specific order or orientation to components of an apparatus is not recited, it is in no way intended that an order or orientation be inferred, in any respect. This holds for any possible non-express basis for interpretation, including: matters of logic with respect to arrangement of steps, operational flow, order of components, or orientation of components; plain meaning derived from grammatical organization or punctuation, and; the number or type of embodiments described in the specification.

As used herein, the singular forms "a," "an" and "the" include plural referents unless the context clearly dictates otherwise. Thus, for example, reference to "a" component includes aspects having two or more such components, unless the context clearly indicates otherwise.

In the embodiments of the hair shine compositions described herein, the amounts of components (e.g., propanediol, dimethyl isosorbide, and the like) are specified in weight per weight percent (wt/wt %), unless otherwise specified.

The terms "0 wt/wt %" and "free," when used to describe the amount and/or absence of a particular component in a hair shine composition, means that the component is not intentionally added to the hair shine composition. However, the hair shine composition may contain traces of the component as a contaminant or tramp in amounts less than 0.05 wt/wt %.

Propanediol has been added to conventional hair compositions, such as shampoos and sprays, to moisturize and soften the hair to which the hair composition is applied. However, these conventional hair compositions do not impart the desired amount of shine, as indicated by a relatively lower refractive index, and strength.

Disclosed herein are hair shine compositions that mitigate the aforementioned problems such that the desired amount of shine and strength may be achieved while retaining moisturizing properties. Specifically, the hair shine compositions disclosed herein include dimethyl isosorbide and propanediol. Dimethyl isosorbide causes the hair shine composition to penetrate the hair and impart a relatively high refractive index, which increases the observable shine. Moreover, the combination of dimethyl isosorbide and propanediol imparts strength to the hair.

The hair shine compositions described herein may be generally described as comprising water, propanediol, and dimethyl isosorbide.

Water is the primary solvent in the hair shine compositions described herein. The amount of water in the hair shine compositions should be sufficiently high (e.g., greater than or equal to 50 wt/wt %) to ensure that the other components of the hair shine composition are sufficiently dissolved or dispersed.

In embodiments, the hair shine composition may comprise greater than or equal to 50 wt/wt % and less than or equal to 95 wt/wt % water. In embodiments, the hair shine composition may comprise greater than or equal to 50 wt/wt % and less than or equal to 75 wt/wt % water. In embodiments, the hair shine composition may comprise greater than or equal to 75 wt/wt % and less than or equal to 95 wt/wt % water. In embodiments, the amount of water in the hair shine composition may be greater than or equal to 50 wt/wt %, greater than or equal to 55 wt/wt %, greater than or equal to 60 wt/wt %, greater than or equal to 65 wt/wt %, greater than or equal to 70 wt/wt %, greater than or equal to 75 wt/wt %, greater than or equal to 80 wt/wt %, greater than or equal to 85 wt/wt %, or even greater than or equal to 90 wt/wt %. In embodiments, the amount of water in the hair shine composition may be less than or equal to 95 wt/wt %, less than or equal to 90 wt/wt %, less than or equal to 85 wt/wt %, less than or equal to 80 wt/wt %, less than or equal to 75 wt/wt %, less than or equal to 70 wt/wt %, or even less than or equal to 65 wt/wt %. In embodiments, the amount of water in the hair shine composition may be greater than or equal to 50 wt/wt % and less than or equal to 95 wt/wt %, greater than or equal to 50 wt/wt % and less than or equal to 90 wt/wt %, greater than or equal to 50 wt/wt % and less than or equal to 85 wt/wt %, greater than or equal to 50 wt/wt % and less than or equal to 80 wt/wt %, greater than or equal to 50 wt/wt % and less than or equal to 75 wt/wt %, greater than or equal to 50 wt/wt % and less than or equal to 70 wt/wt %, greater than or equal to 50 wt/wt % and less than or equal to 65 wt/wt %, greater than or equal to 55 wt/wt % and less than or equal to 95 wt/wt %, greater than or equal to 55 wt/wt % and less than or equal to 90 wt/wt %, greater than or equal to 55 wt/wt % and less than or equal to 85 wt/wt %, greater than or equal to 55 wt/wt % and less than or equal to 80 wt/wt %, greater than or equal to 55 wt/wt % and less than or equal to 75 wt/wt %, greater than or equal to 55 wt/wt % and less than or equal to 70 wt/wt %, greater than or equal to 55 wt/wt % and less than or equal to 65 wt/wt %, greater than or equal to 60 wt/wt % and less than or equal to 95 wt/wt %, greater than or equal to 60 wt/wt % and less than or equal to 90 wt/wt %, greater than or equal to 60 wt/wt % and less than or equal to 85 wt/wt %, greater than or equal to 60 wt/wt % and less than or equal to 80 wt/wt %, greater than or equal to 60 wt/wt % and less than or equal to 75 wt/wt %, greater than or equal to 60 wt/wt % and less than or equal to 70 wt/wt %, greater than or equal to 60 wt/wt % and less than or equal to 65 wt/wt %, greater than or equal to 65 wt/wt % and less than or equal to 95 wt/wt %, greater than or equal to 65 wt/wt % and less than or equal to 90 wt/wt %, greater than or equal to 65 wt/wt % and less than or equal to 85 wt/wt %, greater than or equal to 65 wt/wt % and less than or equal to 80 wt/wt %, greater than or equal to 65 wt/wt % and less than or equal to 75 wt/wt %, greater than or equal to 65 wt/wt % and less than or equal to 70 wt/wt %, greater than or equal to 70 wt/wt % and less than or equal to 95 wt/wt %, greater than or equal to 70 wt/wt % and less than or equal to 90 wt/wt %, greater than or equal to 70 wt/wt % and less than or equal to 85 wt/wt %, greater than or equal to 70 wt/wt % and less than or equal to 80 wt/wt %, greater than or equal to 70 wt/wt % and less than or equal to 75 wt/wt %, greater than or equal to 75 wt/wt % and less than or equal to 95 wt/wt %, greater than or equal to 75 wt/wt % and less than or equal to 90 wt/wt %, greater than or equal to 75 wt/wt % and less than or equal to 85 wt/wt %, greater than or equal to 75 wt/wt % and less than or equal to 80 wt/wt %, greater than or equal to 80 wt/wt % and less than or equal to 95 wt/wt %, greater than or equal to 80 wt/wt % and less than or equal to 90 wt/wt %, greater than or equal to 80 wt/wt % and less than or equal to 85 wt/wt %, greater than or equal to 85 wt/wt % and less than or equal to 95 wt/wt %, greater than or equal to 85 wt/wt % and less than or equal to 90 wt/wt %, or even greater than or equal to 90 wt/wt % and less than or equal to 95 wt/wt %, or any and all sub-ranges formed from any of these endpoints.

As described herein, propanediol moisturizes the hair. A sufficient amount of propanediol (e.g., greater than or equal to 0.5 wt/wt %) should be included such that the hair to which the hair shine composition is applied has the desired amount of softness.

In embodiments, the hair shine composition may comprise greater than or equal to 0.5 wt/wt % and less than or equal to 3 wt/wt % propanediol. In embodiments, the hair shine composition may comprise greater than or equal to 0.5 wt/wt % and less than or equal to 2.5 wt/wt % propanediol. In embodiments, the amount of propanediol in the hair shine composition may be greater than or equal to 0.5 wt/wt %, greater than or equal to 0.6 wt/wt %, greater than or equal to 0.7 wt/wt %, greater than or equal to 0.8 wt/wt %, or even greater than or equal to 0.9 wt/wt %. In embodiments, the amount of propanediol in the hair shine composition may be less than or equal to 3 wt/wt %, less than or equal to 2.5 wt/wt %, less than or equal to 2 wt/wt %, less than or equal to 1.5 wt/wt %, or even less than or equal to 1 wt/wt %. In embodiments, the amount of propanediol in the hair shine composition may be greater than or equal to 0.5 wt/wt % and less than or equal to 3 wt/wt %, greater than or equal to 0.5 wt/wt % and less than or equal to 2.5 wt/wt %, greater than or equal to 0.5 wt/wt % and less than or equal to 2 wt/wt %, greater than or equal to 0.5 wt/wt % and less than or equal to 1.5 wt/wt %, greater than or equal to 0.5 wt/wt % and less than or equal to 1 wt/wt %, greater than or equal to 0.6 wt/wt % and less than or equal to 3 wt/wt %, greater than or equal to 0.6 wt/wt % and less than or equal to 2.5 wt/wt %, greater than or equal to 0.6 wt/wt % and less than or equal to 2 wt/wt %, greater than or equal to 0.6 wt/wt % and less than or equal to 1.5 wt/wt %, greater than or equal to 0.6 wt/wt % and less than or equal to 1 wt/wt %, greater than or equal to 0.7 wt/wt % and less than or equal to 3 wt/wt %, greater than or equal to 0.7 wt/wt % and less than or equal to 2.5 wt/wt %, greater than or equal to 0.7 wt/wt % and less than or equal to 2 wt/wt %, greater than or equal to 0.7 wt/wt % and less than or equal to 1.5 wt/wt %, greater than or equal to 0.7 wt/wt % and less than or equal to 1 wt/wt %, greater than or equal to 0.8 wt/wt % and less than or equal to 3 wt/wt %, greater than or equal to 0.8 wt/wt % and less than or equal to 2.5 wt/wt %, greater than or equal to 0.8 wt/wt % and less than or equal to 2 wt/wt %, greater than or equal to 0.8 wt/wt % and less than or equal to 1.5 wt/wt %, greater than or equal to 0.8 wt/wt % and less than or equal to 1 wt/wt %, greater than or equal to 0.9 wt/wt % and less than or equal to 3 wt/wt %, greater than or equal to 0.9 wt/wt % and less than or equal to 2.5 wt/wt %, greater than or equal to 0.9 wt/wt % and less than or equal to 2 wt/wt %, greater than or equal to 0.9 wt/wt % and less than or equal to 1.5 wt/wt %, or even greater than or equal to 0.9 wt/wt % and less than or equal to 1 wt/wt %, or any and all sub-ranges formed from any of these endpoints.

In embodiments, the hair shine composition may comprise greater than or equal to 0.5 wt/wt % and less than or equal to 15 wt/wt % propanediol. In embodiments, the hair shine composition may comprise greater than or equal to 1 wt/wt % and less than or equal to 13 wt/wt % propanediol. In embodiments, the amount of propanediol in the hair shine composition may be greater than or equal to 0.5 wt/wt %, greater than or equal to 1 wt/wt %, greater than or equal to 3 wt/wt %, or even greater than or equal to 5 wt/wt %. In embodiments, the amount of propanediol in the hair shine composition may be less than or equal to 15 wt/wt %, less than or equal to 13 wt/wt %, or even less than or equal to 10 wt/wt %. In embodiments, the amount of propanediol in the hair shine composition may be greater than or equal to 0.5 wt/wt % and less than or equal to 15 wt/wt %, greater than or equal to 0.5 wt/wt % and less than or equal to 13 wt/wt %, greater than or equal to 0.5 wt/wt % and less than or equal to 10 wt/wt %, greater than or equal to 1 wt/wt % and less than or equal to 15 wt/wt %, greater than or equal to 1 wt/wt % and less than or equal to 13 wt/wt %, greater than or equal to 1 wt/wt % and less than or equal to 10 wt/wt %, greater than or equal to 3 wt/wt % and less than or equal to 15 wt/wt %, greater than or equal to 3 wt/wt % and less than or equal to 13 wt/wt %, greater than or equal to 3 wt/wt % and less than or equal to 10 wt/wt %, greater than or equal to 5 wt/wt % and less than or equal to 15 wt/wt %, greater than or equal to 5 wt/wt % and less than or equal to 13 wt/wt %, or even greater than or equal to 5 wt/wt % and less than or equal to 10 wt/wt %, or any and all sub-ranges formed from any of these endpoints.

Dimethyl isosorbide imparts a relatively low viscosity to the hair shine composition, which causes the hair shine composition to penetrate deeper into individual hair fibers and achieve a relatively higher amount of observable shine as indicated by a relatively higher refractive index of the hair. The amount of dimethyl isosorbide may be tailored to control the viscosity of the hair shine composition. A sufficient amount of dimethyl isosorbide (e.g., greater than or equal to 0.25 wt/wt %) may be included such that the hair shine composition achieves the desired refractive index (i.e., observable shine). However, if the amount of dimethyl isosorbide is too high (e.g., greater than 12 wt/wt %), the viscosity of the hair shine composition may decrease, thereby diminishing the ability of the hair shine composition to remain in the hair.

In embodiments, the hair shine composition may comprise greater than or equal to 0.25 wt/wt % and less than or equal to 2 wt/wt % dimethyl isosorbide. In embodiments, the hair shine composition may comprise greater than or equal to 0.3 wt/wt % and less than or equal to 1.75 wt/wt % dimethyl isosorbide. In embodiments, the amount of dimethyl isosorbide in the hair shine composition may be greater than or equal to 0.25 wt/wt %, greater than or equal to 0.3 wt/wt %, greater than or equal to 0.4 wt/wt %, greater than or equal to 0.5 wt/wt %, or even greater than or equal to 0.6 wt/wt %. In embodiments, the amount of dimethyl isosorbide in the hair shine composition may be less than or equal to 2 wt/wt %, less than or equal to 1.75 wt/wt %, less than or equal to 1.5 wt/wt %, less than or equal to 1.25 wt/wt %, less than or equal to 1 wt/wt %, or even less than or equal to 0.75 wt/wt %. In embodiments, the amount of dimethyl isosorbide in the hair shine composition may be greater than or equal to 0.25 wt/wt % and less than or equal to 2 wt/wt %, greater than or equal to 0.25 wt/wt % and less than or equal to 1.75 wt/wt %, greater than or equal to 0.25 wt/wt % and less than or equal to 1.5 wt/wt %, greater than or equal to 0.25 wt/wt % and less than or equal to 1.25 wt/wt %, greater than or equal to 0.25 wt/wt % and less than or equal to 1 wt/wt %, greater than or equal to 0.25 wt/wt % and less than or equal to 0.75 wt/wt %, greater than or equal to 0.3 wt/wt % and less than or equal to 2 wt/wt %, greater than or equal to 0.3 wt/wt % and less than or equal to 1.75 wt/wt %, greater than or equal to 0.3 wt/wt % and less than or equal to 1.5 wt/wt %, greater than or equal to 0.3 wt/wt % and less than or equal to 1.25 wt/wt %, greater than or equal to 0.3 wt/wt % and less than or equal to 1 wt/wt %, greater than or equal to 0.3 wt/wt % and less than or equal to 0.75 wt/wt %, greater than or equal to 0.4 wt/wt % and less than or equal to 2 wt/wt %, greater than or equal to 0.4 wt/wt % and less than or equal to 1.75 wt/wt %, greater than or equal to 0.4 wt/wt % and less than or equal to 1.5 wt/wt %, greater than or equal to 0.4 wt/wt % and less than or equal to 1.25 wt/wt %, greater than or equal to 0.4 wt/wt % and less than or equal to 1 wt/wt %, greater than or equal to 0.4 wt/wt % and less than or equal to 0.75 wt/wt %, greater than or equal to 0.5 wt/wt % and less than or equal to 2 wt/wt %, greater than or equal to 0.5 wt/wt % and less than or equal to 1.75 wt/wt %, greater than or equal to 0.5 wt/wt % and less than or equal to 1.5 wt/wt %, greater than or equal to 0.5 wt/wt % and less than or equal to 1.25 wt/wt %, greater than or equal to 0.5 wt/wt % and less than or equal to 1 wt/wt %, greater than or equal to 0.5 wt/wt % and less than or equal to 0.75 wt/wt %, greater than or equal to 0.6 wt/wt % and less than or equal to 2 wt/wt %, greater than or equal to 0.6 wt/wt % and less than or equal to 1.75 wt/wt %, greater than or equal to 0.6 wt/wt % and less than or equal to 1.5 wt/wt %, greater than or equal to 0.6 wt/wt % and less than or equal to 1.25 wt/wt %, greater than or equal to 0.6 wt/wt % and less than or equal to 1 wt/wt %, or even greater than or equal to 0.6 wt/wt % and less than or equal to 0.75 wt/wt %, or any and all sub-ranges formed from any of these endpoints.

In embodiments, the hair shine composition may comprise greater than or equal to 0.1 wt/wt % and less than or equal to 12 wt/wt % dimethyl isosorbide. In embodiments, the hair shine composition may comprise greater than or equal to 0.25 wt/wt % and less than or equal to 10 wt/wt % dimethyl isosorbide. In embodiments, the amount of dimethyl isosorbide in the hair shine composition may be greater than or equal to 0.1 wt/wt %, greater than or equal to 0.25 wt/wt %, greater than or equal to 0.5 wt/wt %, greater than or equal to 1 wt/wt %, or even greater than or equal to 3 wt/wt %. In embodiments, the amount of dimethyl isosorbide in the hair shine composition may be less than or equal to 12 wt/wt %, less than or equal to 10 wt/wt %, or even less than or equal to 8 wt/wt %. In embodiments, the amount of dimethyl isosorbide in the hair shine composition may be greater than or equal to 0.1 wt/wt % and less than or equal to 12 wt/wt %, greater than or equal to 0.1 wt/wt % and less than or equal to 10 wt/wt %, greater than or equal to 0.1 wt/wt % and less than or equal to 8 wt/wt %, greater than or equal to 0.25 wt/wt % and less than or equal to 12 wt/wt %, greater than or equal to 0.25 wt/wt % and less than or equal to 10 wt/wt %, greater than or equal to 0.25 wt/wt % and less than or equal to 8 wt/wt %, greater than or equal to 0.5 wt/wt % and less than or equal to 12 wt/wt %, greater than or equal to 0.5 wt/wt % and less than or equal to 10 wt/wt %, greater than or equal to 0.5 wt/wt % and less than or equal to 8 wt/wt %, greater than or equal to 1 wt/wt % and less than or equal to 12 wt/wt %, greater than or equal to 1 wt/wt % and less than or equal to 10 wt/wt %, greater than or equal to 1 wt/wt %, and less than or equal to 8 wt/wt %, greater than or equal to 3 wt/wt % and less than or equal to 12 wt/wt %, greater than or equal to 3 wt/wt % and less than or equal to 10 wt/wt %, or even greater than or equal to 3 wt/wt % and less than or equal to 8 wt/wt %, or any and all sub-ranges formed from any of these endpoints.

In embodiments, a wt/wt % ratio of propanediol to dimethyl isosorbide in the hair shine composition (i.e., propanediol (wt/wt %) to dimethyl isosorbide (wt/wt %) may be from 1.00:1 to 3.00:1 to ensure that the desired refractive index (i.e., observable shine), softness, and strength are achieved. In embodiments, a wt/wt % ratio of propanediol to dimethyl isosorbide in the hair shine composition may be from 1.25:1 to 1.75:1. In embodiments, a wt/wt % ratio of propanediol to dimethyl isosorbide in the hair shine composition may be greater than or equal to 1.00:1, greater than or equal to 1.10:1, greater than or equal to 1.25:1, greater than or equal to 1.30:1, or even greater than or equal to 1.40:1. In embodiments, a wt/wt % ratio of propanediol to dimethyl isosorbide in the hair shine composition may be less than or equal to 3.00:1, less than or equal to 2.75:1, less than or equal to 2.50:1, less than or equal to 2.25:1, less than or equal to 2.00:1, less than or equal to 1.75:1, or even less than or equal to 1.60:1. In embodiments, a wt/wt % ratio of propanediol to dimethyl isosorbide in the hair shine composition may be from 1.00:1 to 3.00:1, from 1.00:1 to 2.75:1, from 1.00:1 to 2.50:1, from 1.00:1 to 2.25:1, from 1.00:1 to 2.00:1, from 1.00:1 to 1.75:1, from 1.00:1 to 1.60:1, from 1.10:1 to 3.00:1, from 1.10:1 to 2.75:1, from 1.10:1 to 2.50:1, from 1.10:1 to 2.25:1, from 1.10:1 to 2.00:1, from 1.10:1 to 1.75:1, from 1.10:1 to 1.60:1, from 1.25:1 to 3.00:1, from 1.25:1 to 2.75:1, from 1.25:1 to 2.50:1, from 1.25:1 to 2.25:1, from 1.25:1 to 2.00:1, from 1.25:1 to 1.75:1, from 1.25:1 to 1.60:1, from 1.30:1 to 3.00:1, from 1.30:1 to 2.75:1, from 1.30:1 to 2.50:1, from 1.30:1 to 2.25:1, from 1.30:1 to 2.00:1, from 1.30:1 to 1.75:1, from 1.30:1 to 1.60:1, from 1.40:1 to 3.00:1, from 1.40:1 to 2.75:1, from 1.40:1 to 2.50:1, from 1.40:1 to 2.25:1, from 1.40:1 to 2.00:1, from 1.40:1 to 1.75:1, or even from 1.40:1 to 1.60:1, or any and all sub-ranges formed from any of these endpoints. In embodiments, a wt/wt % ratio of propanediol to dimethyl isosorbide in the hair shine composition may be 1.50:1.

In embodiments, the hair shine compositions described herein may further comprise isopentyldiol, which acts as a humectant. In embodiments, the hair shine composition may comprise greater than or equal to 0.25 wt/wt % and less than or equal to 2 wt/wt % isopentyldiol. In embodiments, the amount of isopentyldiol in the hair shine composition may be greater than or equal to 0.25 wt/wt %, greater than or equal to 0.3 wt/wt %, greater than or equal to 0.4 wt/wt %, greater than or equal to 0.5 wt/wt %, or even greater than or equal to 0.6 wt/wt. In embodiments, the amount of isopentyldiol in the hair shine composition may be less than or equal to 2 wt/wt %, less than or equal to 1.75 wt/wt %, less than or equal to 1.5 wt/wt %, less than or equal to 1.25 wt/wt %, less than or equal to 1 wt/wt %, or even less than or equal to 0.75 wt/wt %. In embodiments, the amount of isopentyldiol in the hair shine composition may be greater than or equal to 0.25 wt/wt % and less than or equal to 2 wt/wt %, greater than or equal to 0.25 wt/wt % and less than or equal to 1.75 wt/wt %, greater than or equal to 0.25 wt/wt % and less than or equal to 1.5 wt/wt %, greater than or equal to 0.25 wt/wt % and less than or equal to 1.25 wt/wt %, greater than or equal to 0.25 wt/wt % and less than or equal to 1 wt/wt %, greater than or equal to 0.25 wt/wt % and less than or equal to 0.75 wt/wt %, greater than or equal to 0.3 wt/wt % and less than or equal to 2 wt/wt %, greater than or equal to 0.3 wt/wt % and less than or equal to 1.75 wt/wt %, greater than or equal to 0.3 wt/wt % and less than or equal to 1.5 wt/wt %, greater than or equal to 0.3 wt/wt % and less than or equal to 1.25 wt/wt %, greater than or equal to 0.3 wt/wt % and less than or equal to 1 wt/wt %, greater than or equal to 0.3 wt/wt % and less than or equal to 0.75 wt/wt %, greater than or equal to 0.4 wt/wt % and less than or equal to 2 wt/wt %, greater than or equal to 0.4 wt/wt % and less than or equal to 1.75 wt/wt %, greater than or equal to 0.4 wt/wt % and less than or equal to 1.5 wt/wt %, greater than or equal to 0.4 wt/wt % and less than or equal to 1.25 wt/wt %, greater than or equal to 0.4 wt/wt % and less than or equal to 1 wt/wt %, greater than or equal to 0.4 wt/wt % and less than or equal to 0.75 wt/wt %, greater than or equal to 0.5 wt/wt % and less than or equal to 2 wt/wt %, greater than or equal to 0.5 wt/wt % and less than or equal to 1.75 wt/wt %, greater than or equal to 0.5 wt/wt % and less than or equal to 1.5 wt/wt %, greater than or equal to 0.5 wt/wt % and less than or equal to 1.25 wt/wt %, greater than or equal to 0.5 wt/wt % and less than or equal to 1 wt/wt %, greater than or equal to 0.5 wt/wt % and less than or equal to 0.75 wt/wt %, greater than or equal to 0.6 wt/wt % and less than or equal to 2 wt/wt %, greater than or equal to 0.6 wt/wt % and less than or equal to 1.75 wt/wt %, greater than or equal to 0.6 wt/wt % and less than or equal to 1.5 wt/wt %, greater than or equal to 0.6 wt/wt % and less than or equal to 1.25 wt/wt %, greater than or equal to 0.6 wt/wt % and less than or equal to 1 wt/wt %, or even greater than or equal to 0.6 wt/wt % and less than or equal to 0.75 wt/wt %, or any and all sub-ranges formed from any of these endpoints.

In embodiments, the hair shine composition may be formulated for use as a shampoo. In embodiments in which the hair shine composition is formulated for use as a shampoo, the hair shine composition may optionally include a non-sulfate cleanser and be free of sulfates such as sodium laureth sulfate and sodium lauryl sulfate, which may damage color treated hair.

In embodiments in which the hair shine composition is formulated for use as a shampoo, the hair shine composition may further comprise an additive such as, by way of example and not limitation, sodium C14-16 olefin sulfonate 40%; cocamidopropyl betaine; decyl glucoside; cocoglucoside; polyquaternium-7; glycol distearate; cocamide MWA; fragrance; citric acid 50%; guar hydroxypropyltrimonium chloride; hydroxypropyl methylcellulose; polyquaternium-10; lactic acid 88% USP; methylchloroisothiazolinone and methylisothiazolinone; chemical grade sodium chloride; stearoxypropyl dimethylamine; PPG-9; sodium hydroxide 50%; or combinations thereof.

In embodiments in which the hair shine composition is formulated for use as a shampoo, the amount each additive in the hair shine composition may be greater than or equal to 0.001 wt/wt %, greater than or equal to 0.01 wt/wt %, greater than or equal to 0.1 wt/wt %, greater than or equal to 0.5 wt/wt %, greater than or equal to 1 wt/wt %, or even greater than or equal to 5 wt/wt %. In embodiments in which the hair shine composition is formulated for use as a shampoo, the amount of each additive in the hair shine composition may be less than or equal to 15 wt/wt %, less than or equal to 12 wt/wt %, less than or equal to 10 wt/wt %, or even less than or equal to 8 wt/wt %. In embodiments in which the hair shine composition is formulated for use as a shampoo, the amount of each additive in the hair shine composition may be greater than or equal to 0.001 wt/wt % and less than or equal to 15 wt/wt %, greater than or equal to 0.001 wt/wt % and less than or equal to 12 wt/wt %, greater than or equal to 0.001 wt/wt % and less than or equal to 10 wt/wt %, greater than or equal to 0.001 wt/wt % and less than or equal to 8 wt/wt %, greater than or equal to 0.01 wt/wt % and less than or equal to 15 wt/wt %, greater than or equal to 0.01 wt/wt % and less than or equal to 12 wt/wt %, greater than or equal to 0.01 wt/wt % and less than or equal to 10 wt/wt %, greater than or equal to 0.01 wt/wt % and less than or equal to 8 wt/wt %, greater than or equal to 0.1 wt/wt % and less than or equal to 15 wt/wt %, greater than or equal to 0.1 wt/wt % and less than or equal to 12 wt/wt %, greater than or equal to 0.1 wt/wt % and less than or equal to 10 wt/wt %, greater than or equal to 0.1 wt/wt % and less than or equal to 8 wt/wt %, greater than or equal to 0.5 wt/wt % and less than or equal to 15 wt/wt %, greater than or equal to 0.5 wt/wt % and less than or equal to 12 wt/wt %, greater than or equal to 0.5 wt/wt % and less than or equal to 10 wt/wt %, greater than or equal to 0.5 wt/wt % and less than or equal to 8 wt/wt %, greater than or equal to 1 wt/wt % and less than or equal to 15 wt/wt %, greater than or equal to 1 wt/wt % and less than or equal to 12 wt/wt %, greater than or equal to 1 wt/wt % and less than or equal to 10 wt/wt %, greater than or equal to 1 wt/wt % and less than or equal to 8 wt/wt %, greater than or equal to 5 wt/wt % and less than or equal to 15 wt/wt %, greater than or equal to 5 wt/wt % and less than or equal to 12 wt/wt %, greater than or equal to 5 wt/wt % and less than or equal to 10 wt/wt %, or even greater than or equal to 5 wt/wt % and less than or equal to 8 wt/wt %, or any and all sub-ranges formed from any of these endpoints.

In embodiments in which the hair shine composition is formulated for use as a shampoo, the hair shine composition may comprise greater than or equal to 50 wt/wt % and less than or equal to 75 wt/wt % water, greater than or equal to 0.5 wt/wt % and less than or equal to 3 wt/wt % propanediol, greater than or equal to 0.25 wt/wt % and less than or equal to 2 wt/wt % dimethyl isosorbide, and greater than or equal to 0.001 wt/wt % and less than or equal to 49.25 wt/wt % of an additive.

In embodiments in which the hair shine composition is formulated for use as a shampoo, the hair shine composition may comprise greater than or equal to 50 wt/wt % and less than or equal to 75 wt/wt % water, greater than or equal to 0.5 wt/wt % and less than or equal to 15 wt/wt % propanediol, greater than or equal to 0.1 wt/wt % and less than or equal to 12 wt/wt % dimethyl isosorbide, and greater than or equal to 0.001 wt/wt % and less than or equal to 49.25 wt/wt % of an additive.

In embodiments, the hair shine composition may be formulated for use as a spray. For example, in embodiments, the hair shine composition may be delivered from a spray pump.

In embodiments in which the hair shine composition is formulated for use as a spray, the hair shine composition may further comprise an additive such as, by way of example and not limitation, glycerin USP, polyquaternium-11, panthenol (powder), benzoic acid, PVP/DMAPA acrylates copolymer, fragrance, disodium EDTA, sodium hydroxide 50%, citric acid anhydrous USP, polysorbate, or combinations thereof.

In embodiments in which the hair shine composition is formulated for use as a spray, the amount of each additive in the hair shine composition may be greater than or equal to 0.001 wt/wt %, greater than or equal to 0.01 wt/wt %, greater than or equal to 0.1 wt/wt %, greater than or equal to 0.5 wt/wt %, or even greater than or equal to 1 wt/wt %. In embodiments in which the hair shine composition is formulated for use as a spray, the amount of each additive in the hair shine composition may be less than or equal to 5 wt %, less than or equal to 4 wt/wt %, less than or equal to 3 wt %, or even less than or equal to 2 wt/wt %. In embodiments in which the hair shine composition is formulated for use as a spray, the amount of each additive in the hair shine composition may be greater than or equal to 0.001 wt/wt % and less than or equal to 5 wt/wt %, greater than or equal to 0.001 wt/wt % and less than or equal to 4 wt/wt %, greater than or equal to 0.001 wt/wt % and less than or equal to 3 wt/wt %, greater than or equal to 0.001 wt/wt % and less than or equal to 2 wt/wt %, greater than or equal to 0.01 wt/wt % and less than or equal to 5 wt/wt %, greater than or equal to 0.01 wt/wt % and less than or equal to 4 wt/wt %, greater than or equal to 0.01 wt/wt % and less than or equal to 3 wt/wt %, greater than or equal to 0.01 wt/wt % and less than or equal to 2 wt/wt %, greater than or equal to 0.1 wt/wt % and less than or equal to 5 wt/wt %, greater than or equal to 0.1 wt/wt % and less than or equal to 4 wt/wt %, greater than or equal to 0.1 wt/wt % and less than or equal to 3 wt/wt %, greater than or equal to 0.1 wt/wt % and less than or equal to 2 wt/wt %, greater than or equal to 0.5 wt/wt % and less than or equal to 5 wt/wt %, greater than or equal to 0.5 wt/wt % and less than or equal to 4 wt/wt %, greater than or equal to 0.5 wt/wt % and less than or equal to 3 wt/wt %, greater than or equal to 0.5 wt/wt % and less than or equal to 2 wt/wt %, greater than or equal to 1 wt/wt % and less than or equal to 5 wt/wt %, greater than or equal to 1 wt/wt % and less than or equal to 4 wt/wt %, greater than or equal to 1 wt/wt % and less than or equal to 3 wt/wt %, or even greater than or equal to 1 wt/wt % and less than or equal to 2 wt/wt %, or any and all sub-ranges formed from any of these endpoints.

In embodiments in which the hair shine composition is formulated for use as a spray, the hair shine composition may comprise greater than or equal to 75 wt/wt % and less than or equal to 95 wt/wt % water, greater than or equal to 0.5 wt/wt % and less than or equal to 3 wt/wt % propanediol, greater than or equal to 0.25 wt/wt % and less than or equal to 2 wt/wt % dimethyl isosorbide, greater than or equal to 0.25 wt/wt % and less than or equal to 2 wt/wt % isopentyldiol, and greater than or equal to 0.001 wt/wt % and less than or equal to 24 wt/wt % of an additive.

In embodiments in which the hair shine composition is formulated for use as a spray, the hair shine composition may comprise greater than or equal to 75 wt/wt % and less than or equal to 95 wt/wt % water, greater than or equal to 0.5 wt/wt % and less than or equal to 15 wt/wt % propanediol, greater than or equal to 0.1 wt/wt % and less than or equal to 2 wt/wt % dimethyl isosorbide, greater than or equal to 0.25 wt/wt % and less than or equal to 2 wt/wt % isopentyldiol, and greater than or equal to 0.001 wt/wt % and less than or equal to 24 wt/wt % of an additive.

Examples

To enhance the understanding of various embodiments, reference is made to the follow examples, which illustrate various embodiments of the hair shine compositions described herein.

Table 1 shows example spray hair compositions E1 and E2 and comparative spray example hair compositions C1-C6 (in terms of wt/wt %).

TABLE 1

| Examples | E1 | E2 | C1 | C2 |
|---|---|---|---|---|
| propanediol | 0.75 | 0.5 | — | 1.0 |
| dimethyl isosorbide | 0.5 | 0.5 | 1.0 | — |
| dipropylene glycol | — | — | — | — |
| 1,2-dichloroethene | — | — | — | — |
| FINSOLV ® TN | — | — | — | — |
| SilShine 151 Gloss Additive | — | — | — | — |

| Examples | C3 | C4 | C5 | C6 |
|---|---|---|---|---|
| propanediol | — | — | — | — |
| dimethyl isosorbide | — | — | — | — |
| dipropylene glycol | 1.0 | — | — | — |
| 1,2-dichloroethene | — | 1.0 | — | — |
| FINSOLV ® TN | — | — | 1.0 | — |
| SilShine 151 Gloss Additive | — | — | — | 1.0 |

Figure 1:
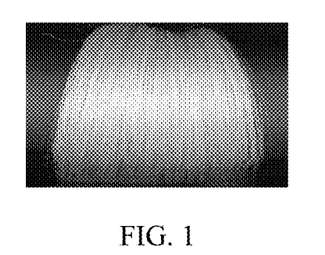
FIG. 1 is a photograph of an untreated bleached tress.
Figure 2:
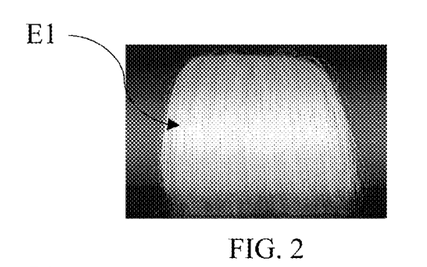
FIG. 2 is a photograph of a bleached tress treated with a hair shine composition according to one or more embodiments described herein.
Figure 3:
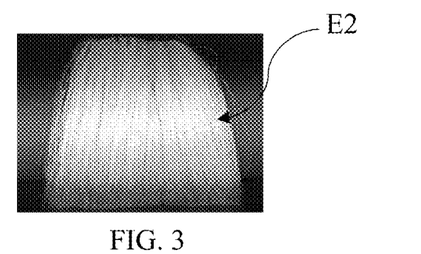
FIG. 3 is a photograph of a bleached tress treated with a hair shine composition according to one or more embodiments described herein.
Figure 4:
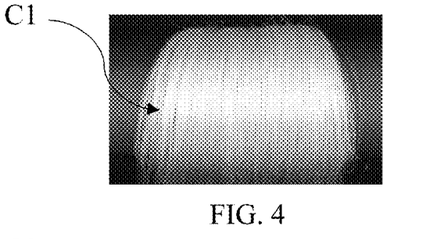
FIG. 4 is a photograph of a bleached tress treated with a comparative hair composition.
Figure 5:
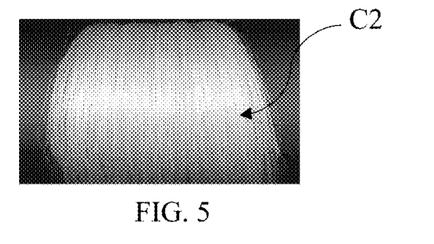
FIG. 5 is a photograph of a bleached tress treated with a comparative hair composition.
Figure 6:
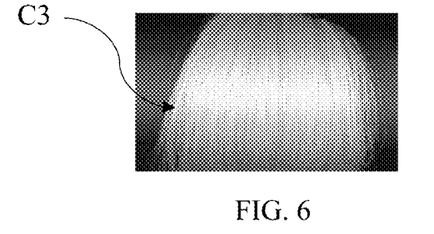
FIG. 6 is a photograph of a bleached tress treated with a comparative hair composition.
Figure 7:
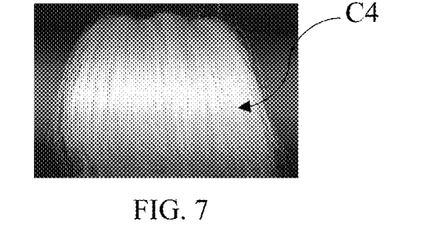
FIG. 7 is a photograph of a bleached tress treated with a comparative hair composition.
Figure 8:
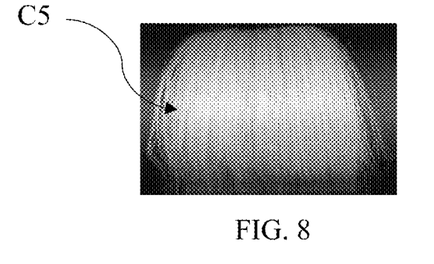
FIG. 8 is a photograph of a bleached tress treated with a comparative hair composition.
Figure 9:
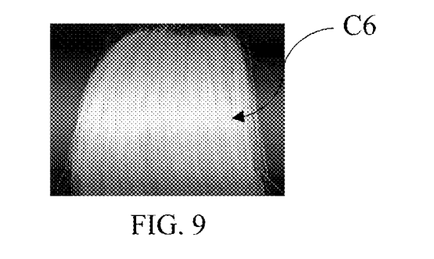
FIG. 9 is a photograph of a bleached tress treated with a comparative hair composition.

FIG. 1 depicts an untreated bleached tress. FIGS. 2-9 depict bleached tresses treated with example spray hair compositions E1 and E2 and comparative example spray hair compositions C1-C6, respectively, for qualitative comparison. As shown in the figures, example spray hair compositions E1 and E2, 1.50:1 and 1.00:1 compositions of propanediol to dimethyl isosorbide, respectively, produced the highest observable amount of shine as compared to comparative spray example hair compositions C1-C6. As indicated by FIGS. 1-9, treating hair with a hair shine composition having a 1.5:1 wt/wt % ratio or a 1:00:1 wt/wt % ratio of propanediol to dimethyl isosorbide results in improved hair shine.

Figure 10:
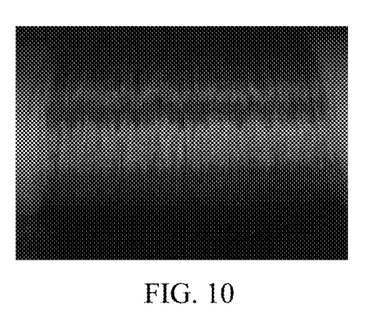
FIG. 10 is a photograph of an untreated brunette tress.
Figure 11:
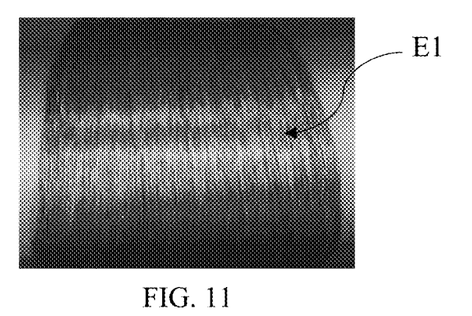
FIG. 11 is a photograph of a brunette tress treated with a hair shine composition according to one or more embodiments described herein.
Figure 12:
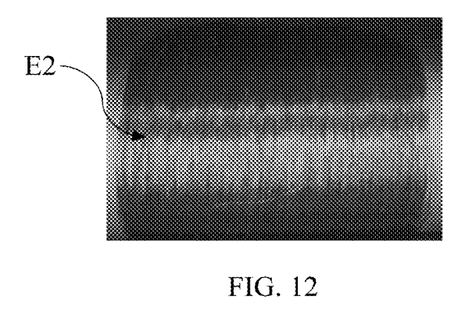
FIG. 12 is a photograph of a brunette tress treated with a hair shine composition according to one or more embodiments described herein.
Figure 13:
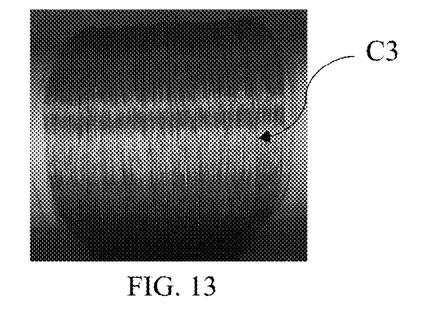
FIG. 13 is a photograph of a brunette tress treated with a comparative hair composition.
Figure 14:
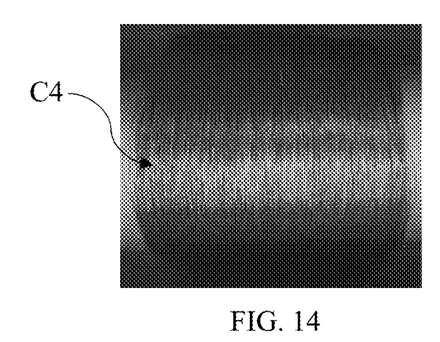
FIG. 14 is a photograph of a brunette tress treated with a comparative hair composition.
Figure 15:
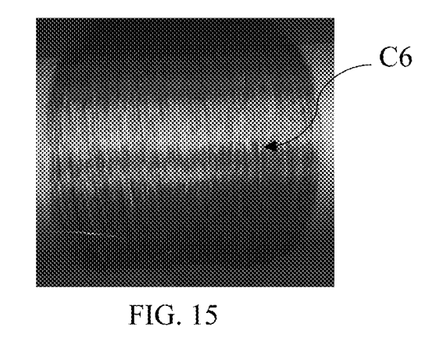
FIG. 15 is a photograph of a brunette tress treated with a comparative hair composition.

FIG. 10 depicts an untreated brunette tress. FIGS. 11-15 depict brunette tresses treated with example hair composition E1 and E2 and comparative example hair compositions C3, C4, and C6, respectively. As shown in the figures, example hair compositions E1 and E2, 1.50:1 and 1.00:1 compositions of propanediol to dimethyl isosorbide, respectively, produced the highest observable amount of shine as compared to comparative example hair compositions C3, C4, and C6. As indicated by FIGS. 10-15, treating hair with a hair shine composition having a 1.50 wt/wt % ratio or a 1:00:1 wt/wt % ratio of propanediol to dimethyl isosorbide results in improved hair shine.

Table 2 shows example spray hair compositions E3 and E4 and comparative spray example hair compositions C7-C14 (in terms of wt/wt %) and the parameters of a breakage study, including hair type, tress weight, and resulting breakage.

To conduct the breakage study, a beaker was filled with the hair composition. A hair tress was submerged in the beaker. The beaker was covered with foil. After 5 minutes, the hair tress was rinsed for 30 seconds in 40° C. water. The hair tress was air dried.

Once the hair tress was dry, the hair tress was secured to a tress tree. The hair tress was combed with a comb 100 times. The comb was placed horizontally to the hair tress and the same combing force was used each time. Once combing was complete, the broken pieces were counted and recorded as shown in Table 2.

TABLE 2

| Examples | E3 | C7 | C8 | C9 | C10 |
|---|---|---|---|---|---|
| Compositions | | | | | |
| propanediol | 9 | — | — | 15 | — |
| dimethyl isosorbide | 6 | — | — | — | 15 |
| deionized water | 85 | 100 | 85 | 85 | 85 |
| propylene glycol | — | — | 15 | — | — |
| Parameters and Results | | | | | |
| Hair Type | untreated tress | untreated tress | untreated tress | untreated tress | untreated tress |
| Tress Weight (g) | 6 | 6 | 6 | 6 | 6 |
| Breakage (number of pieces) | 24 | 126 | 253 | 125 | 51 |

| Examples | E4 | C11 | C12 | C13 | C14 |
|---|---|---|---|---|---|
| Compositions | | | | | |
| propanediol | 9 | — | — | 15 | — |
| dimethyl isosorbide | 6 | — | — | — | 15 |
| deionized water | 85 | 100 | 85 | 85 | 85 |
| propylene glycol | — | — | | — | — |
| Parameters | | | | | |
| Hair Type | bleached tress | bleached tress | bleached tress | bleached tress | bleached tress |
| Tress Weight (g) | 2 | 2 | 2 | 2 | 2 |
| Breakage (number of pieces) | 18 | 125 | 269 | 66 | 48 |

As shown in Table 2, example spray hair compositions E3 and E4, 1.50:1 compositions of propanediol and dimethyl isosorbide, resulted in the lowest amount of breakage as compared to comparative spray example hair compositions C7-C14. As indicated by Table 2, treating hair with a hair shine composition having a 1.50:1 wt/wt % ratio of propanediol to dimethyl isosorbide results in strengthened hair.

Embodiments may be further described with respect to the below clauses:

1. A hair shine composition comprising: greater than or equal to 50 wt/wt % and less than or equal to 95 wt/wt % water; greater than or equal to 0.5 wt/wt % and less than or equal to 3 wt/wt % propanediol; and greater than or equal to 0.25 wt/wt % and less than or equal to 2 wt/wt % dimethyl isosorbide, wherein: a wt/wt % ratio of propanediol to dimethyl isosorbide is from 1.00:1 to 3.00:1.
2. The hair shine composition of any preceding clause, wherein the wt/wt % ratio of propanediol to dimethyl isosorbide is from 1.25:1 to 1.75:1.
3. The hair shine composition of any preceding clause, wherein the hair shine composition further comprises greater than or equal to 0.25 wt/wt % and less than or equal to 2 wt/wt % isopentyldiol.
4. The hair shine composition of any preceding clause, wherein the hair shine composition comprises greater than or equal to 0.5 wt/wt % and less than or equal to 2.5 wt/wt % propanediol.
5. The hair shine composition of any preceding clause, wherein the hair shine composition comprises greater than or equal to 0.3 wt/wt % and less than or equal to 1.75 wt/wt % dimethyl isosorbide.
6. The hair shine composition of any preceding clause, wherein the hair shine composition comprises greater than or equal to 50 wt/wt % and less than or equal to 75 wt/wt % water.
7. The hair shine composition of any preceding clause, wherein the hair shine composition comprises greater than or equal to 75 wt/wt % and less than or equal to 95 wt/wt % water.
8. The hair shine composition of any preceding clause, wherein the hair shine composition is formulated for use as a shampoo.
9. The hair shine composition of any preceding clause, wherein the hair shine composition further comprises a non-sulfate cleanser.
10. The hair shine composition of any preceding clause, wherein the hair shine composition is free of sulfates.
11. The hair shine composition of any preceding clause, wherein the hair shine composition is formulated for use as a spray.
12. The hair shine composition of any preceding clause, wherein the wt/wt % ratio of propanediol to dimethyl isosorbide is 1.50:1.
13. The hair shine composition of any preceding clause, wherein the hair shine composition further comprises greater than or equal to 0.3 wt/wt % and less than or equal to 1.75 wt/wt % isopentyldiol.
14. The hair shine composition of any preceding clause, wherein the hair shine composition further comprises greater than or equal to 0.4 wt/wt % and less than or equal to 1.5 wt/wt % isopentyldiol.
15. The hair shine composition of any preceding clause, wherein the hair shine composition comprises greater than or equal to 0.6 wt/wt % and less than or equal to 2 wt/wt % propanediol.
16. The hair shine composition of any preceding clause, wherein the hair shine composition comprises greater than or equal to 0.7 wt/wt % and less than or equal to 1.5 wt/wt % propanediol.
17. The hair shine composition of any preceding clause, wherein the hair shine composition comprises greater than or equal to 0.4 wt/wt % and less than or equal to 1.5 wt/wt % dimethyl isosorbide.
18. The hair shine composition of any preceding clause, wherein the hair shine composition comprises greater than or equal to 0.5 wt/wt % and less than or equal to 1.25 wt/wt % dimethyl isosorbide.
19. The hair shine composition of any preceding clause, wherein the hair shine composition is formulated for use as a shampoo and the hair shine composition comprises greater than or equal to 50 wt/wt % and less than or equal to 75 wt/wt % water, greater than or equal to 0.5 wt/wt % and less than or equal to 3 wt/wt % propanediol, greater than or equal to 0.25 wt/wt % and less than or equal to 2 wt/wt % dimethyl isosorbide, and greater than or equal to 0.001 wt/wt % and less than or equal to 49.25 wt/wt % of an additive.
20. The hair shine composition of any preceding clause, wherein the hair shine composition is formulated for use as a spray and the hair shine composition comprises greater than or equal to 75 wt/wt % and less than or equal to 95 wt/wt % water, greater than or equal to 0.5 wt/wt % and less than or equal to 3 wt/wt % propanediol, greater than or equal to 0.25 wt/wt % and less than or equal to 2 wt/wt % dimethyl isosorbide, greater than or equal to 0.25 wt/wt % and less than or equal to 2 wt/wt % isopentyldiol, and greater than or equal to 0.001 wt/wt % and less than or equal to 24 wt/wt % of an additive.
21. A hair shine composition comprising: greater than or equal to 50 wt/wt % and less than or equal to 95 wt/wt % water; greater than or equal to 0.5 wt/wt % and less than or equal to 15 wt/wt % propanediol; and greater than or equal to 0.1 wt/wt % and less than or equal to 12 wt/wt % dimethyl isosorbide, wherein: a wt/wt % ratio of propanediol to dimethyl isosorbide is from 1.00:1 to 3.00:1.
22. The hair shine composition of any preceding clause, wherein the wt/wt % ratio of propanediol to dimethyl isosorbide is from 1.25:1 to 1.75:1.
23. The hair shine composition of any preceding clause, wherein the hair shine composition further comprises greater than or equal to 0.25 wt/wt % and less than or equal to 2 wt/wt % isopentyldiol.
24. The hair shine composition of any preceding clause, wherein the hair shine composition comprises greater than or equal to 1 wt/wt % and less than or equal to 13 wt/wt % propanediol.
25. The hair shine composition of any preceding clause, wherein the hair shine composition comprises greater than or equal to 0.25 wt/wt % and less than or equal to 10 wt/wt % dimethyl isosorbide.
26. The hair shine composition of any preceding clause, wherein the hair shine composition comprises greater than or equal to 50 wt/wt % and less than or equal to 75 wt/wt % water.
27. The hair shine composition of any preceding clause, wherein the hair shine composition comprises greater than or equal to 75 wt/wt % and less than or equal to 95 wt/wt % water.
28. The hair shine composition of any preceding clause, wherein the hair shine composition is formulated for use as a shampoo.
29. The hair shine composition of any preceding clause, wherein the hair shine composition further comprises a non-sulfate cleanser.
30. The hair shine composition of any preceding clause, wherein the hair shine composition is free of sulfates.
31. The hair shine composition of any preceding clause, wherein the hair shine composition is formulated for use as a spray.
32. The hair shine composition of any preceding clause, wherein the wt/wt % ratio of propanediol to dimethyl isosorbide is 1.50:1.
33. The hair shine composition of any preceding clause, wherein the hair shine composition further comprises greater than or equal to 0.3 wt/wt % and less than or equal to 1.75 wt/wt % isopentyldiol.
34. The hair shine composition of any preceding clause, wherein the hair shine composition further comprises greater than or equal to 0.4 wt/wt % and less than or equal to 1.5 wt/wt % isopentyldiol.

35. The hair shine composition of any preceding clause, wherein the hair shine composition comprises greater than or equal to 3 wt/wt % and less than or equal to 13 wt/wt % propanediol.
36. The hair shine composition of any preceding clause, wherein the hair shine composition comprises greater than or equal to 5 wt/wt % and less than or equal to 10 wt/wt % propanediol.
37. The hair shine composition of any preceding clause, wherein the hair shine composition comprises greater than or equal to 0.5 wt/wt % and less than or equal to 10 wt/wt % dimethyl isosorbide.
38. The hair shine composition of any preceding clause, wherein the hair shine composition comprises greater than or equal to 1 wt/wt % and less than or equal to 8 wt/wt % dimethyl isosorbide.
39. The hair shine composition of any preceding clause, wherein the hair shine composition is formulated for use as a shampoo and the hair shine composition comprises greater than or equal to 50 wt/wt % and less than or equal to 75 wt/wt % water, greater than or equal to 0.5 wt/wt % and less than or equal to 15 wt/wt % propanediol, greater than or equal to 0.1 wt/wt % and less than or equal to 12 wt/wt % dimethyl isosorbide, and greater than or equal to 0.001 wt/wt % and less than or equal to 49.25 wt/wt % of an additive.
40. The hair shine composition of any preceding clause, wherein the hair shine composition is formulated for use as a spray and the hair shine composition comprises greater than or equal to 75 wt/wt % and less than or equal to 95 wt/wt % water, greater than or equal to 0.5 wt/wt % and less than or equal to 15 wt/wt % propanediol, greater than or equal to 0.1 wt/wt % and less than or equal to 12 wt/wt % dimethyl isosorbide, greater than or equal to 0.25 wt/wt % and less than or equal to 2 wt/wt % isopentyldiol, and greater than or equal to 0.001 wt/wt % and less than or equal to 24 wt/wt % of an additive.

It will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these aspects.

What is claimed is:
1. A hair shine composition comprising:
  greater than or equal to 50 wt/wt % and less than or equal to 95 wt/wt % water;
  greater than or equal to 0.5 wt/wt % and less than or equal to 3 wt/wt % propanediol; and
  greater than or equal to 0.25 wt/wt % and less than or equal to 2 wt/wt % dimethyl isosorbide, wherein:
  a wt/wt % ratio of propanediol to dimethyl isosorbide is from 1.00:1 to 3.00:1.
2. The hair shine composition of claim 1, wherein the wt/wt % ratio of propanediol to dimethyl isosorbide is from 1.25:1 to 1.75:1.
3. The hair shine composition of claim 1, wherein the hair shine composition further comprises greater than or equal to 0.25 wt/wt % and less than or equal to 2 wt/wt % isopentyldiol.
4. The hair shine composition of claim 1, wherein the hair shine composition comprises greater than or equal to 0.5 wt/wt % and less than or equal to 2.5 wt/wt % propanediol.
5. The hair shine composition of claim 1, wherein the hair shine composition comprises greater than or equal to 0.3 wt/wt % and less than or equal to 1.75 wt/wt % dimethyl isosorbide.
6. The hair shine composition of claim 1, wherein the hair shine composition comprises greater than or equal to 50 wt/wt % and less than or equal to 75 wt/wt % water.
7. The hair shine composition of claim 1, wherein the hair shine composition comprises greater than or equal to 75 wt/wt % and less than or equal to 95 wt/wt % water.
8. The hair shine composition of claim 1, wherein the hair shine composition is formulated for use as a shampoo.
9. The hair shine composition of claim 8, wherein the hair shine composition further comprises a non-sulfate cleanser.
10. The hair shine composition of claim 1, wherein the hair shine composition is formulated for use as a spray.
11. A hair shine composition comprising:
  greater than or equal to 50 wt/wt % and less than or equal to 95 wt/wt % water;
  greater than or equal to 0.5 wt/wt % and less than or equal to 15 wt/wt % propanediol; and
  greater than or equal to 0.1 wt/wt % and less than or equal to 12 wt/wt % dimethyl isosorbide, wherein:
  a wt/wt % ratio of propanediol to dimethyl isosorbide is from 1.00:1 to 3.00:1.
12. The hair shine composition of claim 11, wherein the wt/wt % ratio of propanediol to dimethyl isosorbide is from 1.25:1 to 1.75:1.
13. The hair shine composition of claim 11, wherein the hair shine composition further comprises greater than or equal to 0.25 wt/wt % and less than or equal to 2 wt/wt % isopentyldiol.
14. The hair shine composition of claim 11, wherein the hair shine composition comprises greater than or equal to 1 wt/wt % and less than or equal to 13 wt/wt % propanediol.
15. The hair shine composition of claim 11 wherein the hair shine composition comprises greater than or equal to 0.25 wt/wt % and less than or equal to 10 wt/wt % dimethyl isosorbide.
16. The hair shine composition of claim 11, wherein the hair shine composition comprises greater than or equal to 50 wt/wt % and less than or equal to 75 wt/wt % water.
17. The hair shine composition of claim 11, wherein the hair shine composition comprises greater than or equal to 75 wt/wt % and less than or equal to 95 wt/wt % water.
18. The hair shine composition of claim 11, wherein the hair shine composition is formulated for use as a shampoo.
19. The hair shine composition of claim 18, wherein the hair shine composition further comprises a non-sulfate cleanser.
20. The hair shine composition of claim 11, wherein the hair shine composition is formulated for use as a spray.

* * * * *